(12) United States Patent
Su et al.

(10) Patent No.: US 8,977,348 B2
(45) Date of Patent: Mar. 10, 2015

(54) SYSTEMS AND METHODS FOR DETERMINING CARDIAC OUTPUT

(71) Applicant: Covidien LP, Boulder, CO (US)

(72) Inventors: Mark Su, Boulder, CO (US); Lockett Wood, Lyons, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/723,766

(22) Filed: Dec. 21, 2012

(65) Prior Publication Data

US 2014/0180136 A1 Jun. 26, 2014

(51) Int. Cl.
*A61B 5/02* (2006.01)
*A61B 5/029* (2006.01)
*A61B 5/0295* (2006.01)
*A61B 5/00* (2006.01)
*A61B 5/024* (2006.01)
*A61B 5/022* (2006.01)

(52) U.S. Cl.
CPC .............. *A61B 5/029* (2013.01); *A61B 5/0295* (2013.01); *A61B 5/7221* (2013.01); *A61B 5/02416* (2013.01); *A61B 5/022* (2013.01)
USPC ........... 600/479; 600/407; 600/476; 600/478; 600/480

(58) Field of Classification Search
None
See application file for complete search history.

(56) References Cited

U.S. PATENT DOCUMENTS

| | | | |
|---|---|---|---|
| 4,094,308 A | 6/1978 | Cormier | |
| 4,282,655 A | 8/1981 | Tinman | |
| 4,289,141 A | 9/1981 | Cormier | |
| 4,450,527 A | 5/1984 | Sramek | |
| 5,092,339 A | 3/1992 | Geddes | |
| 5,178,151 A | 1/1993 | Sackner | |
| 5,275,159 A | 1/1994 | Griebel | |
| 5,331,960 A | 7/1994 | Krenzke | |
| 5,408,327 A | 4/1995 | Geiler | |
| 5,595,182 A | 1/1997 | Krivitski | |
| 5,743,268 A | 4/1998 | Kabal | |
| 5,817,010 A | 10/1998 | Hibl | |
| 5,833,618 A | 11/1998 | Caro | |
| 5,913,826 A | 6/1999 | Blank | |
| 5,935,066 A | 8/1999 | Harris | |
| 6,004,272 A | 12/1999 | Barry | |
| 6,045,509 A | 4/2000 | Caro | |
| 6,155,984 A | 12/2000 | Krivitski | |

(Continued)

FOREIGN PATENT DOCUMENTS

| | | |
|---|---|---|
| EP | 0 537 383 | 4/1993 |
| EP | 0 841 034 | 5/1998 |

(Continued)

OTHER PUBLICATIONS

"Derivation of Respiratory Signals from Multi-lead ECGS, Moody," et al. (1985).

(Continued)

*Primary Examiner* — Mark Remaly

(57) ABSTRACT

A system is provided including a thoracic bio-impedance or bio-reactance (TBIR) analysis module, a photoplethysmograph (PPG) analysis module, and a cardiac output module. The TBIR module is configured to obtain TBIR information from a TBIR detector, and the PPG analysis module is configured to obtain PPG information from a PPG detector. The cardiac output module is configured to determine the cardiac output of a patient using the TBIR information and the PPG information.

22 Claims, 7 Drawing Sheets

(56) References Cited

U.S. PATENT DOCUMENTS

| | | |
|---|---|---|
| 6,292,686 B1 | 9/2001 | Chaiken |
| 6,371,921 B1 | 4/2002 | Caro |
| 6,389,306 B1 | 5/2002 | Chaiken |
| 6,503,206 B1 | 1/2003 | Li |
| 6,616,613 B1 | 9/2003 | Goodman |
| 6,719,705 B2 | 4/2004 | Mills |
| 6,740,072 B2 | 5/2004 | Starkweather |
| 6,754,523 B2 | 6/2004 | Toole |
| 6,758,822 B2 | 7/2004 | Romano |
| 6,760,608 B2 | 7/2004 | Lynn |
| 6,776,764 B2 | 8/2004 | Pinsky |
| 6,816,266 B2 | 11/2004 | Varshneya |
| 6,869,402 B2 | 3/2005 | Arnold |
| 6,875,176 B2 | 4/2005 | Mourad |
| 7,022,077 B2 | 4/2006 | Mourad |
| 7,033,320 B2 | 4/2006 | Von Behren |
| 7,056,292 B2 | 6/2006 | Hutchinson |
| 7,171,271 B2 | 1/2007 | Koh |
| 7,220,230 B2 | 5/2007 | Roteliuk |
| 7,452,333 B2 | 11/2008 | Roteliuk |
| 7,462,152 B2 | 12/2008 | Kolluri |
| 7,615,011 B2 | 11/2009 | Sugo |
| 7,674,231 B2 | 3/2010 | McCombie |
| 7,704,209 B2 | 4/2010 | Bennett |
| 7,747,301 B2 | 6/2010 | Cheng |
| 7,785,263 B2 | 8/2010 | Roteliuk |
| 7,806,830 B2 | 10/2010 | Bernstein |
| 7,850,617 B2 | 12/2010 | Goedje |
| 7,881,762 B2 | 2/2011 | Kling |
| 7,894,869 B2 | 2/2011 | Hoaran |
| 7,899,510 B2 | 3/2011 | Hoaran |
| 7,976,472 B2 | 7/2011 | Kiani |
| 8,073,516 B2 | 12/2011 | Scharf |
| 8,073,518 B2 | 12/2011 | Chin |
| 8,187,197 B2 | 5/2012 | Shapira |
| 8,211,031 B2 | 7/2012 | Poupko |
| 2002/0022785 A1 | 2/2002 | Romano |
| 2002/0082485 A1 | 6/2002 | Faithfull |
| 2003/0167012 A1 | 9/2003 | Friedman |
| 2005/0080345 A1 | 4/2005 | Finburgh |
| 2005/0085707 A1 | 4/2005 | Maria Korsten et al. |
| 2005/0124903 A1 | 6/2005 | Roteliuk |
| 2005/0240087 A1 | 10/2005 | Keenan |
| 2006/0184051 A1 | 8/2006 | Hempstead |
| 2006/0224053 A1 | 10/2006 | Black |
| 2007/0093702 A1 | 4/2007 | Yu |
| 2007/0213625 A1 | 9/2007 | Nayak |
| 2007/0249949 A1 | 10/2007 | Hadley |
| 2008/0082004 A1 | 4/2008 | Banet |
| 2008/0119329 A1 | 5/2008 | Punkka |
| 2008/0139958 A1 | 6/2008 | Uemura |
| 2008/0183232 A1 | 7/2008 | Voss |
| 2008/0287815 A1 | 11/2008 | Chon |
| 2009/0099459 A1 | 4/2009 | Svanberg |
| 2009/0149762 A1 | 6/2009 | Ou Yang et al. |
| 2009/0177110 A1 | 7/2009 | Lyden |
| 2009/0198140 A1 | 8/2009 | Riobo Aboy et al. |
| 2009/0204012 A1 | 8/2009 | Joeken |
| 2009/0240119 A1 | 9/2009 | Schwaibold |
| 2009/0326353 A1 | 12/2009 | Watson |
| 2009/0326388 A1 | 12/2009 | Watson |
| 2009/0326395 A1 | 12/2009 | Watson |
| 2010/0016739 A1 | 1/2010 | Shelley |
| 2010/0049007 A1 | 2/2010 | Sterling |
| 2010/0049071 A1 | 2/2010 | Goor |
| 2010/0081895 A1 | 4/2010 | Zand |
| 2010/0152547 A1 | 6/2010 | Sterling |
| 2010/0152591 A1 | 6/2010 | Yu |
| 2010/0160794 A1 | 6/2010 | Banet |
| 2010/0191128 A1 | 7/2010 | Shelley |
| 2010/0210924 A1 | 8/2010 | Parthasarathy |
| 2010/0249542 A1 | 9/2010 | Thijs |
| 2010/0249559 A1 | 9/2010 | Lovejoy |
| 2010/0249612 A1 | 9/2010 | Cohen |
| 2010/0268090 A1 | 10/2010 | Rubinstein |
| 2010/0268101 A1 | 10/2010 | Sugo |
| 2010/0268518 A1 | 10/2010 | Sugo |
| 2010/0298689 A1 | 11/2010 | Wang |
| 2010/0324388 A1 | 12/2010 | Moon |
| 2010/0324431 A1 | 12/2010 | Addison |
| 2010/0324827 A1 | 12/2010 | Addison |
| 2011/0009754 A1 | 1/2011 | Wenzel |
| 2011/0009755 A1 | 1/2011 | Wenzel |
| 2011/0026784 A1 | 2/2011 | Van Slyke |
| 2011/0034813 A1 | 2/2011 | Cohen |
| 2011/0040345 A1 | 2/2011 | Wenzel |
| 2011/0060234 A1 | 3/2011 | Zhou |
| 2011/0060531 A1 | 3/2011 | Sugo |
| 2011/0077532 A1 | 3/2011 | Kim |
| 2011/0087115 A1 | 4/2011 | Sackner |
| 2011/0098112 A1 | 4/2011 | LeBoeuf |
| 2011/0098546 A1 | 4/2011 | Farazi |
| 2011/0105918 A1 | 5/2011 | Fortin |
| 2011/0172504 A1 | 7/2011 | Wegerich |
| 2011/0209915 A1 | 9/2011 | Telfort |
| 2011/0224564 A1 | 9/2011 | Moon |
| 2011/0270097 A1 | 11/2011 | Aboy |
| 2011/0301436 A1 | 12/2011 | Teixeira |
| 2012/0022350 A1 | 1/2012 | Teixeira |
| 2012/0029320 A1 | 2/2012 | Watson |
| 2012/0029361 A1 | 2/2012 | Addison |
| 2012/0029363 A1 | 2/2012 | Lund |
| 2012/0046557 A1 | 2/2012 | Kiani |
| 2012/0053433 A1 | 3/2012 | Chamoun |
| 2012/0053469 A1 | 3/2012 | Melker |
| 2012/0065485 A1 | 3/2012 | Benni |
| 2012/0065527 A1 | 3/2012 | Gill |
| 2012/0065528 A1 | 3/2012 | Gill |
| 2012/0078069 A1 | 3/2012 | Melker |
| 2012/0109018 A1 | 5/2012 | Gertner |
| 2012/0136261 A1 | 5/2012 | Sethi |
| 2012/0172723 A1 | 7/2012 | Gertner |

FOREIGN PATENT DOCUMENTS

| | | |
|---|---|---|
| EP | 1 443 856 | 2/2006 |
| EP | 1 769 737 | 4/2007 |
| EP | 1 884 189 | 2/2008 |
| EP | 2 281 508 | 2/2011 |
| EP | 2 047 794 | 2/2012 |
| EP | 2 217 140 | 2/2012 |
| WO | WO 91/13589 | 9/1991 |
| WO | WO 94/14372 | 7/1994 |
| WO | WO 97/47236 | 12/1997 |
| WO | WO 98/41279 | 9/1998 |
| WO | WO 02/03076 | 1/2002 |
| WO | WO 03/082099 | 10/2003 |
| WO | WO 2004/071292 | 8/2004 |
| WO | WO 2005/055825 | 6/2005 |
| WO | WO 2006/100676 | 9/2006 |
| WO | WO 2007/109065 | 9/2007 |
| WO | WO 2008/094598 | 8/2008 |
| WO | WO 2008/144404 | 11/2008 |
| WO | WO 2008/144525 | 11/2008 |
| WO | WO 2009/009761 | 1/2009 |
| WO | WO 2009/014420 | 1/2009 |
| WO | WO 2009/101140 | 8/2009 |
| WO | WO 2010/001231 | 1/2010 |
| WO | WO 2010/045556 | 4/2010 |
| WO | WO 2010/096475 | 8/2010 |
| WO | WO 2010/111073 | 9/2010 |
| WO | WO/2010/124034 | 10/2010 |
| WO | WO 2010/146326 | 12/2010 |
| WO | WO 2010/146327 | 12/2010 |
| WO | WO 2011/047211 | 4/2011 |
| WO | WO 2011/050066 | 4/2011 |
| WO | WO 2011/051822 | 5/2011 |
| WO | WO 2011/060220 | 5/2011 |
| WO | WO 2011/077294 | 6/2011 |
| WO | WO 2011/080190 | 7/2011 |
| WO | WO 2011/080194 | 7/2011 |
| WO | WO2011/087927 | 7/2011 |
| WO | WO 2011/089488 | 7/2011 |
| WO | WO 2012/009350 | 1/2012 |

(56) References Cited

FOREIGN PATENT DOCUMENTS

| WO | WO 2012/014065 | 2/2012 |
|---|---|---|
| WO | WO 2012/015426 | 2/2012 |
| WO | WO 2012/027613 | 3/2012 |
| WO | WO 2012/032413 | 3/2012 |
| WO | WO 2012/032536 | 3/2012 |
| WO | WO 2012/052926 | 4/2012 |
| WO | WO 2012/075322 | 6/2012 |
| WO | WO 2012/076957 | 6/2012 |

OTHER PUBLICATIONS

"Photoplethsmography and its application in clinical physiological measurement," Physiol. Meas. 28 (2007).
"Venus Oximetry," Signa Vitae 2007.
"On the Analysis of Fingertip Photoplethysmogram Signals," Elgendi, Current Cardiology Reviews, 2012.
"A Computer Based Photoplethysmographic Vascular Analyzer Through Derivatives," Gonzalez, et al, Computers in Cardiology (2008).
"Noninvasive Assessment of the Digital Volume Pulse: Comparison with the Peripheral Pressure Pulse," Millasseau, et al., Journal of the American Heart Association (2000).
"Non-Invasive Estimation of Cardiac Output from Finger Photoplethysmogram Based on Windkessel Model," Poon, Bulletin of Advance Technology Research, vol. 4, No. 6 (2010).
"Non-constrained Blood Pressure Monitoring Using ECG and PPG for Personal Healthcare," Yoon, et al, (2008).
"How to measure heart rate?" Vogel, et al. Eur. J. Clin Paramacol (2004) 60.461-466.
"Resting Heart Rate in Cardiovascular Disease," Fox, et al. Journal of the Amercan College of Cardiology vol. 50, No. 9 (2007).
"Why measure resting heart rate?" Nauman (2012).
"The shape and dimensions of photoplethsymographic pulse waves; a measurement repeatability study," Marcinkevics, et al. Acta Universitatis Latviensis,vol. 753, Bilology, pp. 99-106 (2009).
"Monitoring of Reactive Hyperemia Using Photoplethysmographic Pulse Amplitude and Transit Time," Selvavaj, et al. Journal of Clinical Monitoring and Computing 23:315-322 (2009).
"Photoacoustic thermal diffusion flowmetry," Sheinfeld, et al., Biomedical Optics Express vol. 3, No. 4 (2012).
"Flow dependent photothermal modulation of the photoacoustic response," Sheinfeld, et al, Photonos Plus Ultrasound: Imaging and Sensing (2012).
"Relation between repiratory variations in pulse oximetry plethysmographic waveform amplitude and arterial pulse pressure in ventilated patients," Cannesson, et al. Ciritical Care (2005).
"Pulse oximeter plethysmograph variation and its relationship to the arterial waveform in mechanically ventilated childer," Chandler, et al. J. Clin. Monit. Comput. (2012).
"Variations in Arterial Blood Pressure and Photoplethysmography During Mechanical Ventilation," Natalani, et al., Technology, Computing, and Simulation, vol. 103, No. 5, (2006).

SYSTEMS AND METHODS FOR DETERMINING CARDIAC OUTPUT

FIELD

Embodiments of the present disclosure generally relate to physiological signal processing, and more particularly, to processing signals to determine the cardiac output of a patient.

BACKGROUND

Cardiac output is the volume of blood pumped by the heart over a given time period. Cardiac output may be divided by body surface area to account for the size of a patient. Cardiac output may be used to assess the state of a patient's circulation. Simple measurements, such as heart rate and/or blood pressure, may be adequate to understand cardiac output for some patients, but more detailed measurements may be required, for example, in the event of any cardiovascular abnormality. Hypotension or low blood pressure may occur in a wide range of patients (for example, due to low cardiac output), especially those in intensive care or postoperative high dependency units. Measurement of cardiac output may be useful to establish a patient's initial cardiovascular state or to measure the patient's response to various therapeutic interventions. However, current methods of measuring cardiac output suffer from a variety of drawbacks. For example, arterial catheters used in measuring cardiac output are highly invasive. As another example, collection of exhaled gases may be used to measure cardiac output, but accurate collection may be difficult due to leaks around a facemask or mouthpiece.

Further, conventional non-invasive techniques suffer from drawbacks as well. For example, conventional non-invasive techniques for determining cardiac output may suffer from inaccuracy, and may often overly involve the use of guesswork or approximations in arriving at cardiac output.

SUMMARY

Certain embodiments of the present disclosure provide a system that may include a thoracic bio-impedance or bio-reactance (TBIR) analysis module, a photoplethysmograph (PPG) analysis module, and a cardiac output module. The TBIR module is configured to obtain TBIR information from a TBIR detector, and the PPG analysis module is configured to obtain PPG information from a PPG detector. The cardiac output module is configured to determine the cardiac output of a patient using the TBIR information and the PPG information.

The TBIR analysis module may include a TBIR cardiac output determining module configured to determine a TBIR-based cardiac output. The PPG analysis module may include a PPG cardiac output determining module configured to determine a PPG-based cardiac output.

The cardiac output module may be configured to determine the cardiac output using at least one of a combination or a comparison of the TBIR-based cardiac output and the PPG-based cardiac output. Further, the cardiac output module may be configured to select one of the TBIR-based cardiac output and the PPG-based cardiac output using TBIR signal quality information and PPG signal quality information.

In some embodiments, the cardiac output module is configured to combine the TBIR-based cardiac output and the PPG-based cardiac output using TBIR signal quality information and PPG signal quality information.

The TBIR cardiac output determining module may be configured to use at least a portion of the PPG information to determine the TBIR-based cardiac output, and the PPG cardiac output determining module may be configured to use at least a portion of the TBIR information to determine the PPG-based cardiac output.

The cardiac output module may be configured to use blood pressure information obtained from a blood pressure detector to determine the cardiac output of the patient. In some embodiments, the system may include a cuff detector for detecting the blood pressure information.

Certain embodiments provide a method for determining cardiac output of a patient. The method may include obtaining thoracic bio-impedance or bio-reactance (TBIR) information from a TBIR detector configured to detect TBIR activity of the patient. The method also may include obtaining photoplethysmographic (PPG) information form a PPG detector configured to detect PPG activity of the patient. Further, the method may include determining, at a processing unit, the cardiac output of the patient using the TBIR information and the PPG information.

Certain embodiments provide a tangible and non-transitory computer readable medium including one or more computer software modules. The one or more computer software modules are configured to direct a processor to obtain thoracic bio-impedance or bio-reactance (TBIR) information from a TBIR detector configured to detect TBIR activity of a patient. Also, the one or more computer software modules are configured to direct a processor to obtain photoplethysmographic (PPG) information from a PPG detector configured to detect PPG activity of the patient. Further, the one or more computer software modules are configured to direct a processor to determine a cardiac output of the patient using the TBIR information and the PPG information.

Embodiments provide for the determination of cardiac output using information from a plurality of different measurement techniques, thereby benefiting from advantages and/or minimizing the effects of disadvantages of the particular individual techniques. Embodiments provide for the use of a plurality of cardiac outputs determined through different measurement and/or calculation approaches to provide a hybrid or composite cardiac output that provides an improved measure of cardiac output than could be obtained using only a single approach. Embodiments thus provide for improved determination of cardiac output. Embodiments also provide for system and methods that are configured to allow for accurate determination of cardiac output that may overcome confounding events that would adversely affect an approach using only a single technique. Further, embodiments provide for sharing information across different technique-based approaches, thereby improving the cardiac output determined by any given technique.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

DETAILED DESCRIPTION

Figure 1:
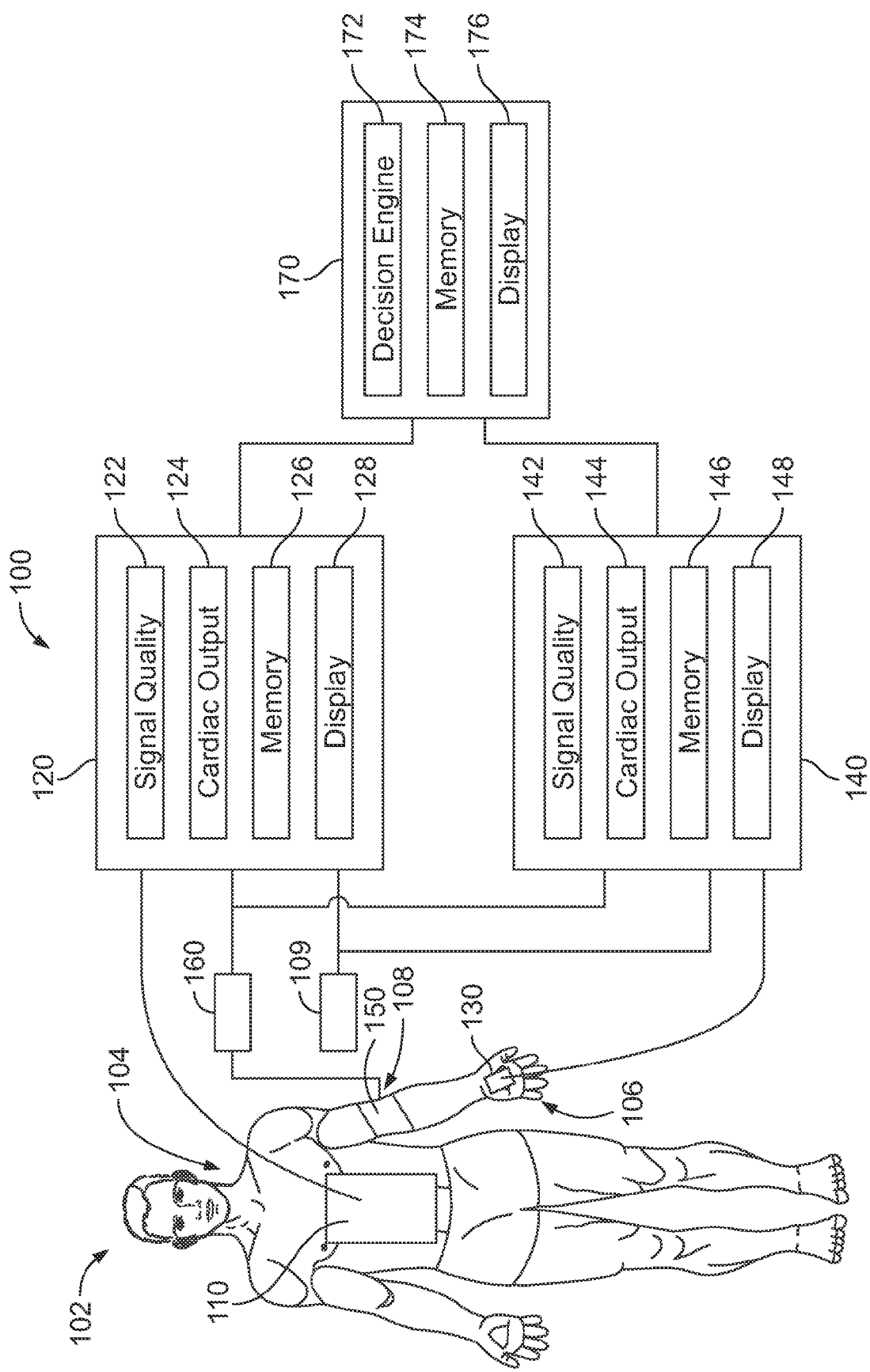
FIG. 1 illustrates a schematic diagram of a system for determining cardiac output according to an embodiment.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments provide for improved determination of technique-based cardiac output (e.g., a cardiac output based primarily upon a given measurement approach such as thoracic bio-impedance or bio-reactance, or, as another example, a photoplethysmogram) by the sharing of information across two or more types of measurement approaches. Embodiments also provide for improved determination of cardiac output by using a plurality of technique-based cardiac outputs to arrive at a determined hybrid or composite cardiac output, for example, by a combination of a plurality of technique-based cardiac outputs, or as another example, by a selection of an appropriate cardiac output from among the plurality of technique-based cardiac outputs. The combination or comparison may be performed using signal quality metrics representative of the quality of the respective technique-based cardiac outputs. Thus, embodiments are able to select (or weight more heavily in a combination) the technique-based cardiac output that provides an accurate representation for a given set of circumstances. For example, a confounding event may adversely affect one measurement approach more adversely than a different approach. By selecting (or weighting more heavily) a technique-based cardiac output less affected by the confounding event than a different technique-based cardiac output more affected by the confounding event, an improved determination of cardiac output may be provided.

For example, thoracic bio-impedance or bio-reactance (TBIR, a measure of the impedance in the thorax of a patient) detection and photoplethysmogram (PPG) detection may be confounded by different events, and provide regarding different physiological events, so a combination of the two approaches may be used to take advantage of aspects where a given technique is advantageous, and/or to minimize aspects where a given technique is less useful. An event or condition that tends to confound TBIR detection (e.g., edema) may not confound PPG detection. Thus, a composite approach using both techniques may rely entirely or primarily on detected PPG information when edema (which tends to confound TBIR detection) is present. Similarly, an event that tends to confound PPG detection (e.g., motion of a finger) may not confound TBIR detection, and the composite approach may instead rely entirely or primarily on detected TBIR information in such circumstances.

In some embodiments, a first technique, using a first group of measurements detected by a first detector system, is used to determine a first cardiac output. For example, the first group of measurements may include measurements of TBIR, which may also be known as thoracic bio-impedance or thoracic bio-reactance. As used herein, unless expressly specified otherwise, the term TBIR includes bio-impedance as well as bio-reactance, which may be considered two different techniques for determining cardiac output using an electrical current measured by transthoracic electrodes. For example, bio-impedance may be considered a measure of electrical change (e.g., resistance) occurring with changing fluid levels in the thorax, while bio-reactance may be considered as tracking a phase of electrical currents through the chest or thorax. A second technique, using a second group of measurements detected by a second detector system, is used to determine a second cardiac output. For example, the second group of measurements may include measurement of a PPG of a patient. Further, one or more of the first or second techniques may not be limited to using information from the respective first or second detector. For example, the first and/or second technique may also employ information obtained from a third detector (e.g., blood pressure), or, additionally or alternatively, the first technique may also use at least a portion of the information obtained via the second technique, and vice versa. By sharing information, each technique may benefit from information obtained more effectively or accurately by the other technique.

FIG. 1 illustrates a schematic diagram of a system 100 for determining cardiac output according to an embodiment. The system 100, for example, may be used in conjunction with embodiments or aspects of methods or systems described elsewhere herein. The system 100 includes a patient information module 109, a TBIR detector 110, a TBIR analysis module 120, a PPG detector 130, a PPG analysis module 140, a blood pressure detector 150, a blood pressure module 160, and a cardiac output module 170. In the illustrated embodiment, the system 100 includes three physiological detectors, namely, the TBIR detector 110, the PPG detector 130, and the blood pressure detector 150. In alternate embodiments, more, fewer, additional, or different physiological detectors (and associated modules may be employed). In alternate embodiments, one or more of the various detectors and/or modules may be combined into integral units. Further, some or all of the various modules of the system 100 may be incorporated into a multiparameter medical monitor.

The various systems, monitors, modules, and units disclosed herein may include a controller, such as a computer processor or other logic-based device that performs operations based on one or more sets of instructions (e.g., software). The instructions on which the controller operates may be stored on a tangible and non-transitory (e.g., not a transient signal) computer readable storage medium, such as a memory. The memory may include one or more computer hard drives, flash drives, RAM, ROM, EEPROM, and the like. Alternatively, one or more of the sets of instructions that direct operations of the controller may be hard-wired into the logic of the controller, such as by being hard-wired logic formed in the hardware of the controller.

In the embodiment illustrated in FIG. 1, a patient 102 is shown being monitored by the system 100. The patient information module 109 is configured as a repository of information regarding the patient 102, and may include information such as height, age, weight, and/or gender of the patient 102, as well as information regarding any particular conditions, characteristics, or medical history of the patient 102 that may be pertinent to the determination of cardiac output. In some embodiments, the patient information module 109 is configured as a stand-alone module that may be accessed by other modules of the system 100, while in other embodiments the patient information module 109 may be incorporated into one or more other modules of the system 100, such as the TBIR analysis module 120, the PPG analysis module 140, and/or the cardiac output module 170.

The TBIR detector 110 is shown attached to the patient 102 at a first region 104 of the patient 102, and is configured to sense one or more outputs or characteristics of cardiac activity of the patient 102, and to provide information representative of the sensed characteristics to the TBIR module 120. For example, the TBIR detector 110 may comprise a plurality of electrodes positioned about the thorax and neck of the patient 102. The TBIR detector 110 may measure the bio-impedance or bio-reactance of the thorax of the patient 102 by measuring changes in the voltage of a signal passed between the electrodes of the TBIR detector 110. The thoracic bio-impedance (Z) of the patient 102 is related to the voltage and current (supplied, for example, by electrodes of the TBIR detector) by the relationship $V=i \times Z$, where V is the voltage, i is the current, and Z is the impedance.

The impedance generally corresponds to the volume of blood in the thorax (the impedance is indirectly proportional to the volume of blood), and thus changes in the impedance generally correspond to changes in the volume of blood in the first region 104 of the patient 102. (See also FIG. 3 and related discussion). Generally speaking, blood has a low impedance (e.g., is a generally good conductor) and air has a high impedance (e.g., is a generally poor conductor), so that the more blood is observed in the thorax, the lower the value of impedance will be detected by the TBIR detector 110. Changes in the impedance may generally correspond to changes in the amount of blood in the heart, which may be used to determine the stroke volume for the patient 102.

The TBIR detector may provide information in the form of a TBIR waveform corresponding to the impedance (Z) of the patient 102 through one or more heart cycles. FIG. 2a illustrates an example of a TBIR waveform 200 over a heart cycle. The TBIR waveform includes a peak 202 and a bottom 204. The bottom 204 generally corresponds to an ending portion of the QRS complex (or depolarization of the heart as the ventricles contract, ejecting blood from the heart, causing the aorta to expand and increasing blood in the thorax), as the thorax has a generally high amount of blood (and corresponding low impedance), and the peak 202 corresponds to a portion of the T wave (or re-polarization of the heart as the ventricles fill with blood) for the depicted heart cycle, as the thorax has a generally low amount of blood (and corresponding high impedance).

The difference between the peak 202 and the bottom 204 is depicted as ΔZ in FIG. 2a. The difference ΔZ corresponds to the difference in the volume of blood being pumped through the heart, and thus may be used to determine stroke volume.

Returning to FIG. 1, the PPG detector 130 is shown attached to the patient 102 at a second region 106 of the patient 102, and is configured to sense one or more outputs or characteristics of cardiac activity of the patient 102, and to provide information representative of the sensed characteristics to the PPG module 140. For example, the PPG detector 130 may comprise a pulse oximetry sensor positioned proximate an extremity, such as a fingertip of the patient 102. As additional, example, a PPG detector may be positioned proximate to a toe, or to the forehead of a patient. The PPG detector 130 may measure an amount of oxygen in the skin, or oxygen saturation at an extremity. (See also FIGS. 4 and 5, and related discussion). In alternate embodiments, the PPG detector 130 may be replaced or supplemented with a different type of detector or detectors, such as a different type of plethysmography detector.

Figure 2B:
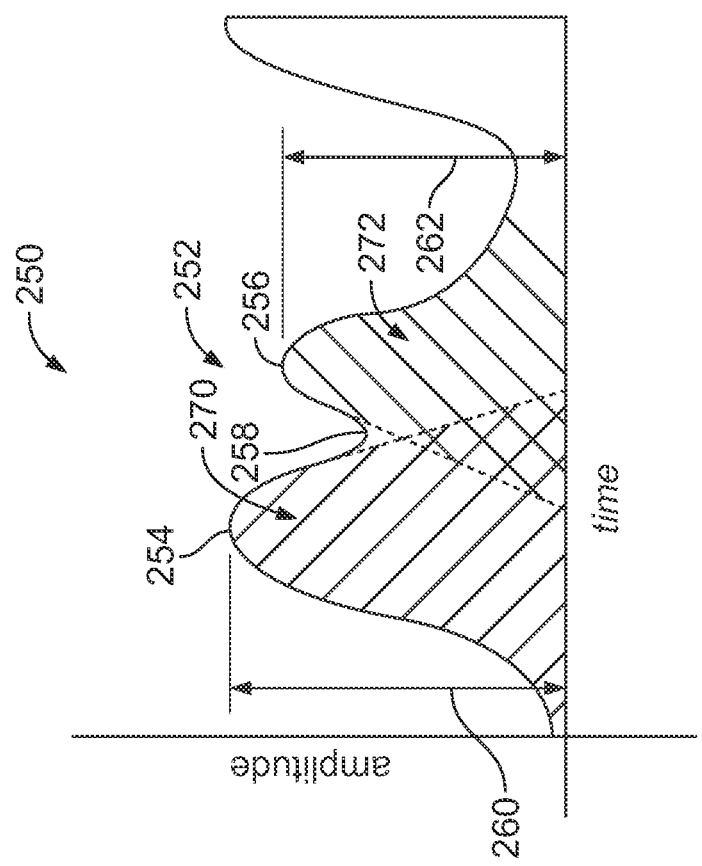
FIG. 2b illustrates a photoplethysmogram (PPG) signal according to an embodiment.
Figure 2A:
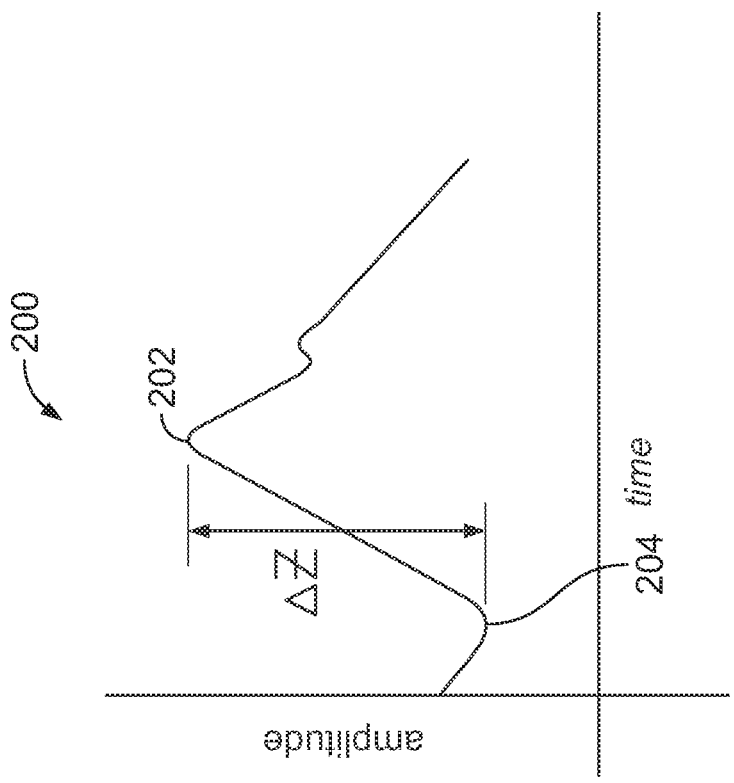
FIG. 2a illustrates a thoracic bio-impedance or bio-reactance (TBIR) signal according to an embodiment.

FIG. 2b illustrates a PPG signal 250 in accordance with an embodiment. In FIG. 2b, the PPG signal 250 shows a single pulse 252. The PPG signal 250 may however include a plurality of pulses over a predetermined time period. The time period may be a fixed time period, or the time period may be variable. Moreover, the time period may be a rolling time period, such as a 5 second rolling timeframe.

Each pulse (e.g., 252) may represent a single heartbeat and may include a pulse-transmitted or primary peak 254 separated from a pulse-reflected or trailing peak 256 by a dichrotic notch 258. The primary peak 254 represents a pressure wave generated from the heart to the point of detection, such as in a finger where the PPG sensor 412 (shown in FIG. 4) is positioned. The trailing peak 256 represents a pressure wave that is reflected from the location proximate where the PPG sensor 412 is positioned back toward the heart. One or more features of the PPG signal 250, such as one or more trailing peaks 256 and one or more primary peaks 254, may be used to identify a portion of a PPG signal corresponding to a physiological cycle.

The blood pressure detector 150 is shown attached to the patient 102 at a third region 108 of the patient 102, and is configured to sense one or more outputs or characteristics of cardiac activity of a patient, and to provide information representative of the sensed characteristics to the blood pressure module 160. The blood pressure detector 150 may comprise a cuff positioned about a limb, for example, an upper arm of the patient 102. The blood pressure detector 150 may measure an arterial pressure of the patient 102, such as a mean arterial pressure (MAP). In some embodiments, the blood pressure detector 150 is used to obtain an average or mean value of blood pressure over a given period of time, while in other embodiments the blood pressure detector 150 is used to obtain generally continuously varying information corresponding to blood pressure, for example a waveform corresponding to arterial blood pressure. The pulse character may vary based on the age and/or physiology of the patient.

The TBIR analysis module 120 is configured to receive TBIR information from the TBIR detector 110 and to determine a TBIR-based value of cardiac output using the TBIR information. The TBIR-based value of cardiac output is an example of a technique-based cardiac output. The TBIR analysis module 120 includes a TBIR signal quality module 122, a TBIR cardiac output determining module 124, a memory 126, and a display module 128. In the illustrated embodiment, the TBIR analysis module 120 is depicted as a stand-alone unit including various modules, such as a TBIR cardiac output determining module 124 and a display module 128. In some embodiments, all or a portion of the TBIR analysis module 120 may be incorporated into other components, such as the cardiac output module 170, or, as another example, a multi-parameter medical monitor. In some embodiments, one or more modules of the TBIR analysis module 120 may be shared with one or more other components or aspects of a medical monitoring system.

The TBIR signal quality module 122 is configured to obtain TBIR information, for example by receiving TBIR information from the TBIR detector 110, and to determine one or more TBIR signal quality metrics for the TBIR information. The signal quality metrics may correspond to characteristics of a given signal, additional physiological measurements or characteristics of the patient 102, and/or characteristics of the particular detection equipment used. For example, the TBIR signal quality module 122 may analyze the TBIR information and determine a signal-to-noise ratio. The TBIR information may also be analyzed to determine the presence and/or amount of one or more artifacts, such as motion related artifacts (for example, corresponding to a change in posture), and one or more signal quality metrics may be determined based on the one or more artifacts. As another example, positive end expiratory pressure (PEEP, a positive pressure utilized during pulmonary ventilation) has been found to affect TBIR measurements in ventilated patients. Thus, in some embodiments, a signal quality metric that represents or accounts for PEEP or variations in PEEP may be used. Signal quality metrics representative of or corresponding to obesity, presence of pleural fluid, chest wall edema, or pulmonary edema may also be used in some embodiments.

Signal quality metrics associated with specific types of detection equipment may be empirically determined and utilized. Further, one or more signal quality metrics may be determined from a comparison of obtained measurements with an expected range or ranges of values for the measurements. If the obtained measurements differ substantially from the expected value, the signal quality metric based on such a comparison may be given a relatively low value, while the signal quality metric may be given a relatively high value if the obtained measurements correspond well with the expected values.

The TBIR cardiac output determining module 124 is configured to obtain TBIR information, for example by receiving the TBIR information from the TBIR detector 110, and to determine a TBIR-based cardiac output using the TBIR information. In some embodiments, the TBIR cardiac output determining module 124 may use information from additional detectors, such as the PPG detector 130 and/or the blood pressure detector 150 to determine the TBIR-based cardiac output.

By way of example, the TBIR cardiac determining module 124 may determine a TBIR-based cardiac output using the relationship CO=PR×SV, where CO is the cardiac output, PR is the pulse rate, and SV is the stroke volume. The TBIR cardiac determining module 124 may first use information from the TBIR detector 110 to determine the SV of the patient 102. As discussed above, the difference $\Delta Z$ of the TBIR waveform 200 corresponds to the difference in the volume of blood being pumped through the heart and thorax, and thus may be used to determine SV (stroke volume). For example, in some embodiments, the difference $\Delta Z$ is used to determine SV via an empirically derived calibration curve obtained in clinical studies, using $\Delta Z$ and mean arterial pressure (MAP) (for example, a MAP value obtained from the blood pressure detector 150) as inputs to arrive at SV, through, for example, a formula, or, as another example, through a look-up table.

The specific formula (e) and/or look-up table(s) may be derived during clinical studies, with $\Delta Z$ and MAP measured along with SV determined by conventional methods (for example, use of an arterial catheter), and the values correlated. The particular formula or table used may vary across patient populations defined, for example, by age, gender, size, and/or other patient characteristics. Thus, in the illustrated embodiment, the TBIR cardiac determining module 124 may be configured to obtain patient characteristic information from the medical record module 109, use the patient characteristic information to determine the appropriate table or formula to be used in determining SV, and then use the appropriate table or formula to determine SV. In some embodiments, the $\Delta Z$ and MAP used may be average values obtained over a given number of cardiac cycles or over a given time period. In some embodiments, a similar clinical study may be used to train a neural network that may subsequently be used to determine values of SV based on correlations experienced during the clinical study.

With SV determined, the TBIR-based cardiac output may be determined. From above, the relationship CO=PR×SV may be used. PR (pulse rate) may be determined in different ways in different embodiments. For example, PR (pulse rate) may be determined using information from the TBIR detector 110. As another example, PR may be determined using information from the PPG detector 130. Thus, the TBIR analysis module 120 may use information from other sensors or detectors in addition to the TBIR detector 110, such as the PPG detector 130. Thus, in some embodiments, the TBIR analysis module may use at least a portion of PPG information obtained via the PPG detector 130 to determine the TBIR-based cardiac output. As another example, PR may be obtained from an electrocardiogram detection system (not shown) attached to the patient 102.

The memory 126 is configured for use by one or more other aspects of the TBIR analysis module 120. Any suitable computer-readable media may be used in the system for data storage. Computer-readable media may be configured to store information that may be interpreted, for example, by a microprocessor. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The display module 128 is configured to provide a display of measured TBIR information and/or the TBIR-based cardiac output. For example, the display module 128 may include a screen that displays TBIR information, such as a TBIR waveform representing the thoracic bio-impedance or bio-reactance (or related parameter) for one or more cardiac cycles. Additionally, or alternatively, the display module 128 may display a value of a TBIR-based cardiac output for a given time period.

The PPG analysis module 140 is configured to receive PPG information from the PPG detector 130 and to determine a PPG-based value of cardiac output using the PPG information, for example, as discussed below. The PPG-based of cardiac output provides another example of a technique-based cardiac output in addition to the TBIR-based cardiac output discussed above. The PPG analysis module 140 includes a PPG signal quality module 142, a PPG cardiac output determining module 144, a memory 146, and a display module 148. In the illustrated embodiment, the PPG analysis module 140 is depicted as a stand-alone unit including various modules, such as a PPG cardiac output determining module 144 and a display module 148. In some embodiments, all or a portion of the PPG analysis module 140 may be incorporated into other components, such as the cardiac output module 170, or, as another example, a multi-parameter medical monitor. In some embodiments, one or more modules of the PPG analysis module 140 may be shared with one or more other components or aspects of a medical monitoring system.

The PPG signal quality module 142 is configured to obtain PPG information, for example, by receiving PPG information from the PPG detector 130, and to determine one or more PPG signal quality metrics for the PPG information. The signal quality metrics may correspond to characteristics of a given signal, additional physiological measurements or characteristics of the patient 102, and/or characteristics of the particular detection equipment used. For example, the PPG signal quality module 142 may analyze the PPG information and determine a signal-to-noise ratio. The PPG information may also be analyzed to determine the presence and/or amount of one or more artifacts, such as motion related artifacts (for example, corresponding to a movement of a finger to which a pulse oximeter is attached), and one or more signal quality metrics may be determined based on the one or more artifacts. As another example, changes in blood flow caused by, for example, changes in temperature and/or certain medications being taken by a patient have been found to affect PPG measurements in patients. Thus, in some embodiments, a signal quality metric that represents or accounts for variations in temperature may be used. Signal quality metrics representative of or corresponding to medications being taken that have been found to affect PPG may be used additionally or alternatively in some embodiments.

Signal quality metrics associated with specific types of detection equipment may be empirically determined and utilized. Further, one or more signal quality metrics may be determined from a comparison of obtained measurements with an expected range or ranges of values for the measurements. The signal quality metric may indicate an amount of match or correspondence of the measured waveform with an expected waveform. If the obtained measurements differ substantially from the expected value, the signal quality metric based on such a comparison may be given a generally low value, while the signal quality metric may be given a relatively high value if the obtained measurements correspond well with the expected values. For example, a PPG waveform for a given cardiac cycle may be expected to have a double bump shape as depicted in FIG. 2b. However, if one or more measured PPG waveforms differ substantially from such a shape, a signal quality metric may be employed indicating that the PPG information is of poor quality.

The PPG cardiac output determining module 144 is configured to obtain PPG information, for example by receiving the PPG information from the PPG detector 130, and to determine a PPG-based cardiac output using the PPG information. In some embodiments, the PPG cardiac output determining module 144 may use information from additional detectors, such as the TBIR detector 110 and/or the blood pressure detector 150 to determine the PPG-based cardiac output.

By way of example, the PPG cardiac determining module 144 may determine a PPG-based cardiac output using the previously discussed relationship CO=PR×SV, where CO is the cardiac output, PR is the pulse rate, and SV is the stroke volume. In some embodiments, the PPG cardiac determining module 144 may further employ the relationship SV=PR× SVR/MAP, where SVR is the systemic vascular resistance, and MAP is the mean arterial pressure (obtained, for example, via the blood pressure detector 150).

For example, in some embodiments, the PPG cardiac determining module 144 determines at least one of SV and/or SVR using information comparing the height of and/or the area under the primary peak 254 and the height of and/or area under the trailing peak 256 of the PPG signal 250. As shown in FIG. 2b, the primary peak 256 has a primary height 260 and a primary area 270, and the trailing peak 254 has a trailing height 262 and a trailing area 272. One or more ratios comparing features of the primary peak 254 and the trailing peak 256 may correspond to the relative size of the primary wave and the reflected wave, and therefore provide insight into the vascular resistance. In some embodiments, the particular ratio or ratios employed (e.g., primary area 270/trailing area 272, primary height 260/trailing height 262) are determined via an empirically derived calibration obtained in clinical studies, using one or more such ratios as inputs to arrive at SVR, through, for example, a formula, or, as another example, through a look-up table.

The specific formula (e) and/or look-up table(s) may be derived during clinical studies, with the heights and areas of the primary and reflected portions of the PPG measured along with SVR determined by conventional methods, and the values correlated. The particular correlation values may vary across patient populations defined, for example, by age, gender, size, and/or other patient characteristics. Thus, in the illustrated embodiment, the PPG cardiac determining module 144 may be configured to obtain patient characteristic information from the medical record module 109, use the patient characteristic information to determine the appropriate table or formula to be used in determining SVR, and then use the appropriate table or formula to determine SVR. In some embodiments, the ratios used may be average values obtained over a given number of cardiac cycles or over a given time period. In some embodiments, a similar clinical study may be used to train a neural network that may subsequently be used to determine values of SVR based on correlations experienced during the clinical study between SVR and one or more ratios of the primary and trailing peaks.

With SVR determined, SV may be determined using the above mentioned relationship SV=PR×SVR/MAP. Pulse rate may be determined, for example, by analyzing the time between the primary peaks of a series of sequential PPG waveforms. MAP may be obtained, for example, via the blood pressure detector 150. Thus, in some embodiments, the PPG analysis module 140 may use information from other sensors or detectors in addition to the PPG detector 130. As another example, the PPG analysis module 140 may use a combination of the SV determined by the TBIR analysis module 120 (or, as another example, a value of SVR determined using the SV determined by the TBIR analysis module 120) to determine a composite SVR value, which in turn may be used to determine SV and/or cardiac output. Thus, in some embodiments, the PPG analysis module 140 may use at least a portion of TBIR information obtained via the TBIR detector 110 to determine the PPG-based cardiac output.

With SV determined, the PPG-based cardiac output may be determined. From above, the relationship CO=PR×SV may be used. PR (pulse rate) may be determined in different ways in different embodiments. For example, PR (pulse rate) may be determined using information from the PPG detector 130.

The memory 146 is configured for use by one or more other aspects of the PPG analysis module 140. Any suitable computer-readable media may be used in the system for data storage. Computer-readable media may be configured to store information that may be interpreted, for example, by a microprocessor. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The display module 148 is configured to provide a display of measured PPG information and/or the PPG-based cardiac output. For example, the display module 148 may include a screen that displays PPG information, such as a PPG waveform representing the PPG for one or more cardiac cycles. Additionally, or alternatively, the display module 148 may display a value of a PPG-based cardiac output for a given time period.

In the illustrated embodiment, the blood pressure module 160 is configured to receive information from the blood pressure detector 150, and to provide information regarding the blood pressure of the patient 102 to the TBIR analysis module 120 and the PPG analysis module 140. The blood pressure module 160 may process raw information received from the blood pressure detector 150. For example, the blood pressure module may determine one or more of a systolic pressure, diastolic pressure, or mean arterial pressure over a given number of cardiac cycles or for a given amount of time. In some embodiments, the blood pressure information may be provided to the TBIR analysis module 120 or the PPG analysis module 140 as a mean or average pressure corresponding to a representative value for a given period, while in other embodiments the blood pressure module 160 may determine and provide a waveform corresponding to the blood pressure plotted against time. In some embodiments, the blood pressure module 160 may be a stand-alone unit, while in other embodiments, the blood pressure module 160 and the blood pressure detector 150 may be an essentially integral unit. In still other embodiments, the blood pressure module 160 may be a component of a medical monitor, such as a multi-parameter medical monitor, or, as another example, the blood pressure module 160 may be a component of the cardiac output module 170.

The cardiac output module 170 is configured to receive information from the TBIR analysis module 120 and the PPG analysis module 140, and to use the information to determine the cardiac output of the patient, for example a hybrid or composite cardiac output. For example, in the illustrated embodiment, the cardiac output module receives the TBIR-based cardiac output, the TBIR signal quality metrics, the PPG-based cardiac output, and the PPG signal quality metrics, and uses the received information to determine a cardiac output for the patient 102.

The cardiac output module 170 includes a decision engine module 172, a memory 174 and a display module 176. In the illustrated embodiment, the cardiac output module 170 is depicted as a stand-alone unit including various modules, such as a decision engine module 172 and a display module 176. In some embodiments, all or a portion of the cardiac output module 170 may be incorporated into other components, such as a multi-parameter medical monitor. In some embodiments, one or more modules of the cardiac output module 170 may be shared with one or more other components or aspects of a medical monitoring system.

Generally speaking, the decision engine module 172 of the cardiac output module 170 obtains TBIR information and PPG information and determines the cardiac output of the patient using the TBIR information and the PPG information. In some embodiments, the cardiac output module 170 may obtain TBIR and PPG information directly from TBIR and PPG detectors, respectively. Alternatively or additionally, the cardiac output module 170 may obtain TBIR and PPG information indirectly from the sensors, for example by receiving a TBIR-based cardiac output determined using the TBIR information and a PPG-based cardiac output determined using the PPG information.

In the illustrated embodiment, the decision engine module 172 obtains the TBIR-based cardiac output and the PPG-based cardiac output along with the corresponding signal metrics from the TBIR analysis module 120 and the PPG analysis module 140, respectively, and determines a hybrid or composite cardiac output based on a comparison and/or a combination of the TBIR-based cardiac output and the PPG cardiac output. For example, in some embodiments, the decision engine module 172 is configured to select from a plurality of technique-based cardiac outputs based on which technique-based approach has one or more better signal quality metrics. For instance, the decision engine module 172 may select one of the TBIR-based cardiac output or the PPG-based cardiac output based on the particular cardiac output that has better signal quality metrics. Alternatively or additionally, the decision engine module 172 may combine the TBIR-based cardiac output and the PPG-based cardiac output to provide a composite cardiac output, with each component of the composite cardiac output given a weighting based on the relative values of one or more signal quality metrics.

As indicated above, the decision engine module 172 may select one technique-based cardiac output from a plurality of technique-based cardiac outputs. As one example, if the TBIR information has a high signal-to-noise ratio along with a waveform shape and amplitude that corresponds well with the expected TBIR waveform, and if the PPG information has a low signal-to-noise ratio along with a waveform shape and amplitude that corresponds poorly with the expected PPG waveform, then the TBIR signal quality metrics will indicate a higher quality of information than the PPG signal quality metrics, and the cardiac output module 170 may select the TBIR-based cardiac output determined by the TBIR analysis module 120 as the cardiac output. Other signal quality metrics or combinations of signal quality metrics may be employed in other embodiments.

As also indicated above, the decision engine module 172 may combine a plurality of technique-based cardiac outputs, for example using a weighting based on signal quality metrics. For example, in some embodiments, if the signal quality metrics of a PPG-based cardiac output are twice as favorable as the signal quality metrics of a TBIR-based cardiac output, than the PPG-based cardiac output may be weighted twice as heavily in a combination. The above is meant by way of example only, as more mathematically complicated combinations and weightings may be used in some embodiments.

For example, in some embodiments, the particular weightings or coefficients employed in a combination based on one or more signal quality metrics may be empirically determined. For example, a calibrated formula or look-up table determined during a clinical trial may be employed. In some embodiments, a neural network may be trained during a clinical trial to associate objectively measured cardiac output values (e.g., measured via an arterial catheter) with a variety of measured signal quality metrics and technique-based cardiac outputs or other technique related values. The appropriately configured neural network may then subsequently be used to determine cardiac output when provided with the measured signal quality metrics and technique-based cardiac output values as inputs.

Generally speaking, appropriately selected and/or weighted signal quality metrics may be employed to determine which of the technique-based cardiac outputs provides a better representation over a given period of time, with that particular technique-based cardiac output either selected as the cardiac output or weighted more heavily in a combination providing the determined cardiac output. For example, for a patient with edema, where a presence of fluid other than blood in the thorax impairs the accuracy of the TBIR-based approach, a PPG approach may be selected or weighted more heavily. As another example, for a patient who has received medication adversely affecting the accuracy of the PPG-based approach, the TBIR-based approach may be selected or weighted more heavily. As yet another example, if, due to sensor malfunction, disengagement for the patient, or any other reason, one of the approaches provides a poor signal-to-noise ratio or otherwise suspect information, the cardiac output determined based on a different approach may be selected or weighted more heavily. Thus, in some embodiments, redundancy is also provided to improve reliability of determined cardiac output in the event of a sensor or detector malfunction.

The memory 174 is configured for use by one or more other aspects of the cardiac output module 170. Any suitable computer-readable media may be used in the system for data storage. Computer-readable media may be configured to store information that may be interpreted, for example, by a microprocessor. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The display module 176 is configured to provide a display of the determined cardiac output. For example, the display module 176 may include a screen that displays the determined cardiac output as well as one or more of the technique-based cardiac outputs used to determine the cardiac output. In some embodiments, one or more of the display modules 128, 148, or 176 may be integrated into a single display unit.

Figure 3:
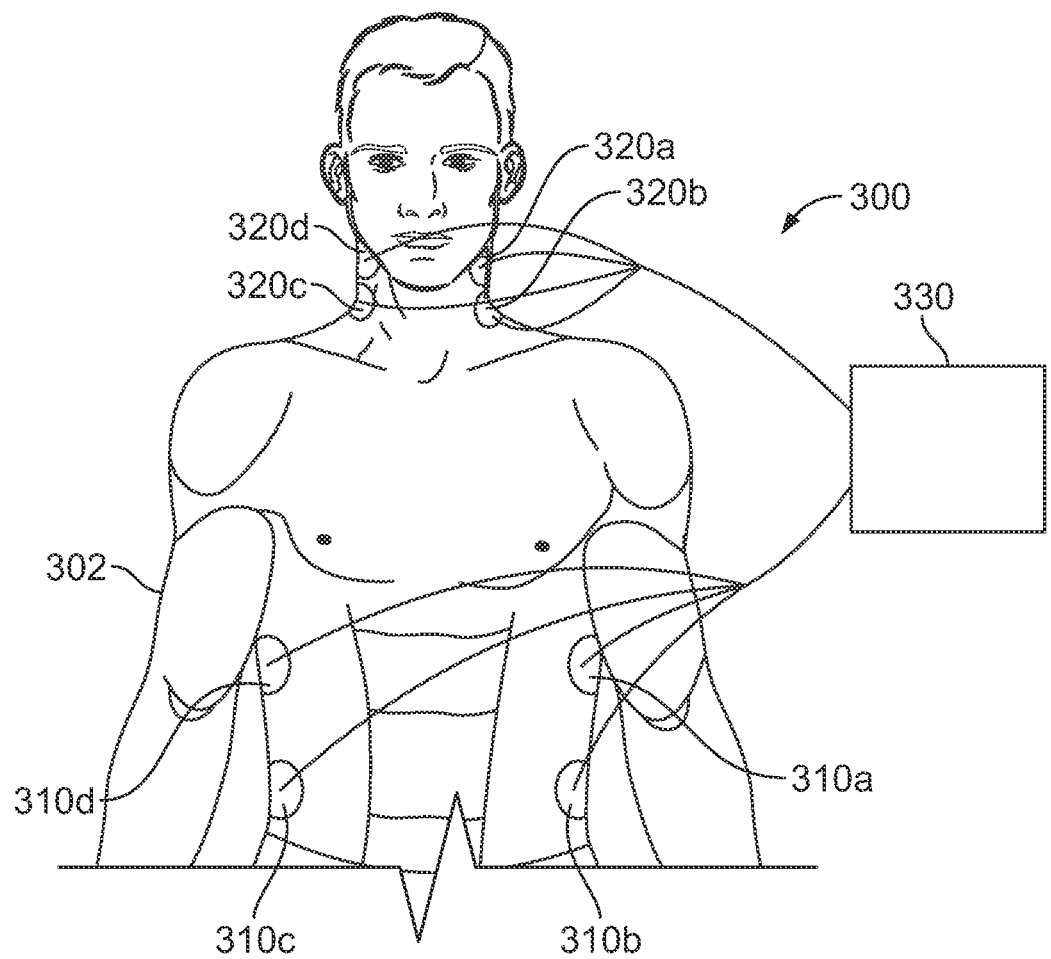
FIG. 3 illustrates a view of a TBIR system according to an embodiment.

FIG. 3 illustrates a plan view of a TBIR sensing system 300 configured to monitor the TBIR of a patient 302, according to an embodiment. The TBIR sensing system 300 includes thoracic electrodes 310a-d, neck electrodes 320a-d, and monitoring unit 330. The monitoring unit 330 is configured to receive information from the thoracic electrodes 310a-d and the neck electrodes 320a-d, and determine TBIR information representative of the physiological activity of the patient 302. For example, the monitoring unit 330 may be substantially similar to the TBIR analysis module 120 discussed above.

The thoracic electrodes 310a-d are positioned on the thorax of the patient 302 generally as shown in FIG. 3. Similarly, the neck electrodes 320a-d are positioned on the neck of the patient 302 generally as shown in FIG. 3. Current is transmitted between the electrodes and used to measure the bio-impedance or bio-reactance of the chest.

Generally speaking, the TBIR sensing system 300 operates as follows. Current is transmitted between the thoracic electrodes 310a-d and the neck electrodes 320a-d. As the cardiac cycle progresses, the volume of blood in the region through which the current passes changes. As the volume of blood increases (e.g., as the thorax fills with blood), the impedance drops (as blood is a generally good conductor), which may be measured as a decrease in voltage across the electrodes. As the volume of blood decreases (e.g., as the blood exits out of the thorax and toward other portions of the body), the impedance increases, which may be measured as an increase in voltage across the electrodes. The monitoring unit 330 may then calculate the impedance over time using known or measured values for current and voltage, and plot the impedance as a TBIR waveform, such as the TBIR waveform 200 depicted in FIG. 2a. In other embodiments, the impedance or TBIR may be determined with different electrode arrangements, or by other measurement techniques.

Figure 4:
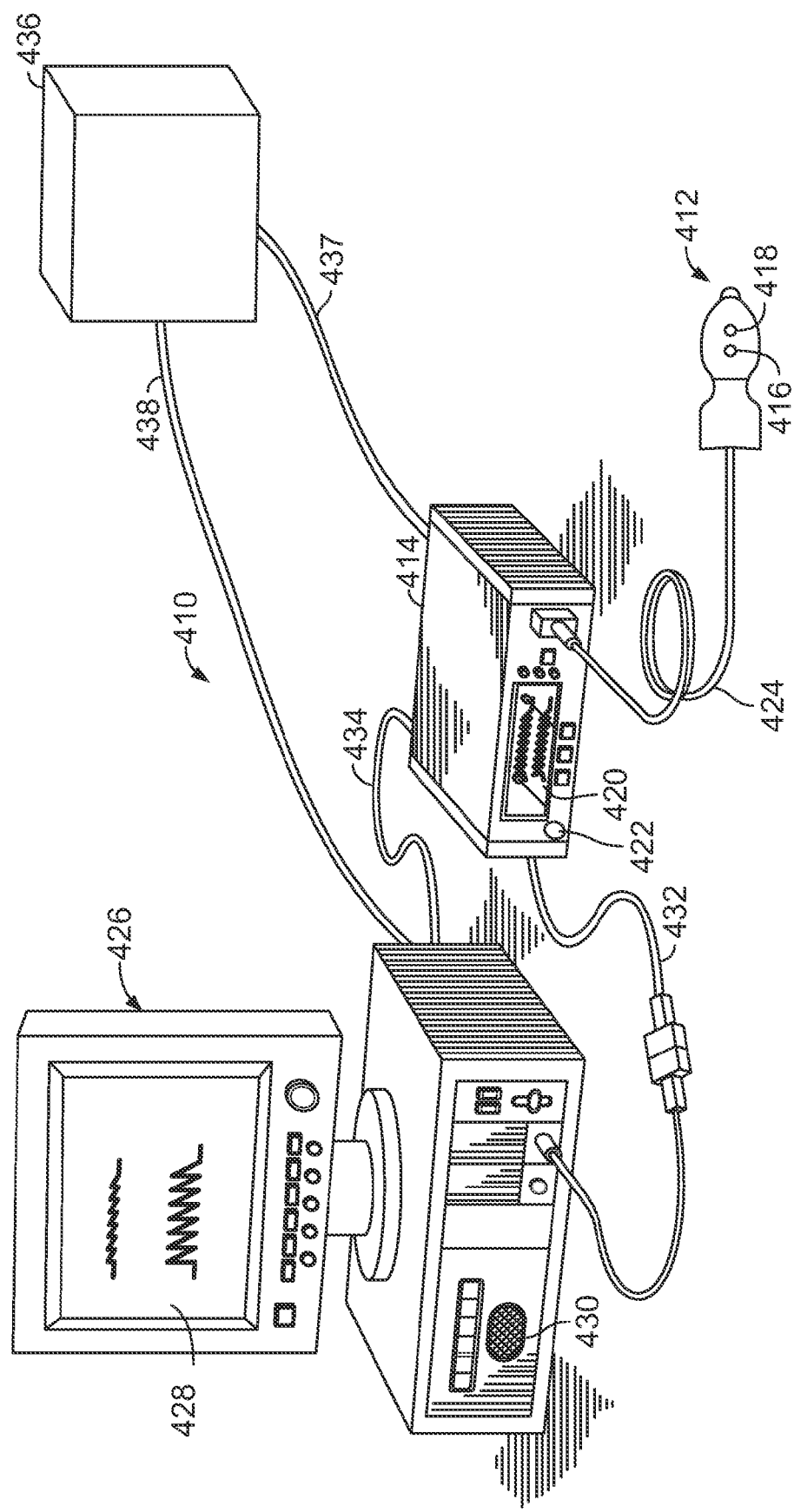
FIG. 4 illustrates an isometric view of a PPG system according to an embodiment.

FIG. 4 illustrates an isometric view of a physiological detection system 410 according to an embodiment. For example, in the illustrated embodiment, the PPG detector 130 and the PPG analysis module 140 may be configured as a PPG system 410. The PPG system 410 may be a pulse oximetry system, for example. Other measurement techniques may be employed in alternate embodiments. The PPG system 410 may include a PPG sensor 412 and a PPG monitor 414. The PPG sensor 412 may include an emitter 416 configured to emit light into tissue of a patient. For example, the emitter 416 may be configured to emit light at two or more wavelengths into the tissue of the patient. The PPG sensor 412 may also include a detector 418 that is configured to detect the emitted light from the emitter 416 that emanates from the tissue after passing through the tissue.

The PPG system 410 may include a plurality of sensors forming a sensor array in place of the PPG sensor 412. Each of the sensors of the sensor array may be a complementary metal oxide semiconductor (CMOS) sensor, for example. Alternatively, each sensor of the array may be a charged coupled device (CCD) sensor. In another embodiment, the sensor array may include a combination of CMOS and CCD sensors. The CCD sensor may include a photoactive region and a transmission region configured to receive and transmit, while the CMOS sensor may include an integrated circuit having an array of pixel sensors. Each pixel may include a photodetector and an active amplifier.

The emitter 416 and the detector 418 may be configured to be located at opposite sides of a digit, such as a finger or toe, in which case the light that is emanating from the tissue passes completely through the digit. The emitter 416 and the detector 418 may be arranged so that light from the emitter 416 penetrates the tissue and is reflected by the tissue into the detector 418, such as a sensor designed to obtain pulse oximetry data.

The sensor 412 or sensor array may be operatively connected to and draw power from the monitor 414. Optionally, the sensor 412 may be wirelessly connected to the monitor 414 and include a battery or similar power supply (not shown). The monitor 414 may be configured to calculate physiological parameters based at least in part on data received from the sensor 412 relating to light emission and detection. Alternatively, the calculations may be performed by and within the sensor 412 and the result of the oximetry reading may be passed to the monitor 414. Additionally, the monitor 414 may include a display 420 configured to display the physiological parameters or other information about the PPG system 410. The monitor 414 may also include a speaker 422 configured to provide an audible sound that may be used in various other embodiments, such as for example, sounding an audible alarm in the event that physiological parameters are outside a predefined normal range.

The sensor 412, or the sensor array, may be communicatively coupled to the monitor 414 via a cable 424. Alternatively, a wireless transmission device (not shown) or the like may be used instead of, or in addition to, the cable 424.

The PPG system 410 may also include a multi-parameter workstation 426 operatively connected to the monitor 414. The workstation 426 may be or include a computing sub-system 430, such as standard computer hardware. The computing sub-system 430 may include one or more modules and control units, such as processing devices that may include one or more microprocessors, microcontrollers, integrated circuits, memory, such as read-only and/or random access memory, and the like. The workstation 426 may include a display 428, such as a cathode ray tube display, a flat panel display, such as a liquid crystal display (LCD), light-emitting diode (LED) display, a plasma display, or any other type of monitor. The computing sub-system 430 of the workstation 426 may be configured to calculate physiological parameters and to show information from the monitor 414 and from other medical monitoring devices or systems (not shown) on the display 428. For example, the workstation 426 may be configured to display an estimate of a patient's blood oxygen saturation generated by the monitor 414 (referred to as an $SpO_2$ measurement), pulse rate information from the monitor 414 and blood pressure from a blood pressure monitor (not shown) on the display 428.

The monitor 414 may be communicatively coupled to the workstation 426 via a cable 432 and/or 434 that is coupled to a sensor input port or a digital communications port, respectively and/or may communicate wirelessly with the workstation 426. Additionally, the monitor 414 and/or workstation 426 may be coupled to a network to enable the sharing of information with servers or other workstations. The monitor 414 may be powered by a battery or by a conventional power source such as a wall outlet.

The PPG system 410 may also include a fluid delivery device 436 that is configured to deliver fluid to a patient. The fluid delivery device 436 may be an intravenous line, an infusion pump, any other suitable fluid delivery device, or any combination thereof that is configured to deliver fluid to a patient. The fluid delivered to a patient may be saline, plasma, blood, water, any other fluid suitable for delivery to a patient, or any combination thereof. The fluid delivery device 436 may be configured to adjust the quantity or concentration of fluid delivered to a patient.

The fluid delivery device 436 may be communicatively coupled to the monitor 414 via a cable 437 that is coupled to a digital communications port or may communicate wirelessly with the workstation 426. Alternatively, or additionally, the fluid delivery device 436 may be communicatively coupled to the workstation 426 via a cable 438 that is coupled to a digital communications port or may communicate wirelessly with the workstation 426. Alternatively or additionally, the fluid delivery device 436 may be communicatively coupled to one or more other aspects of a fluid responsiveness determination system, such as a fluid responsiveness analysis module or ventilator unit similar to those discussed elsewhere herein.

Figure 5:
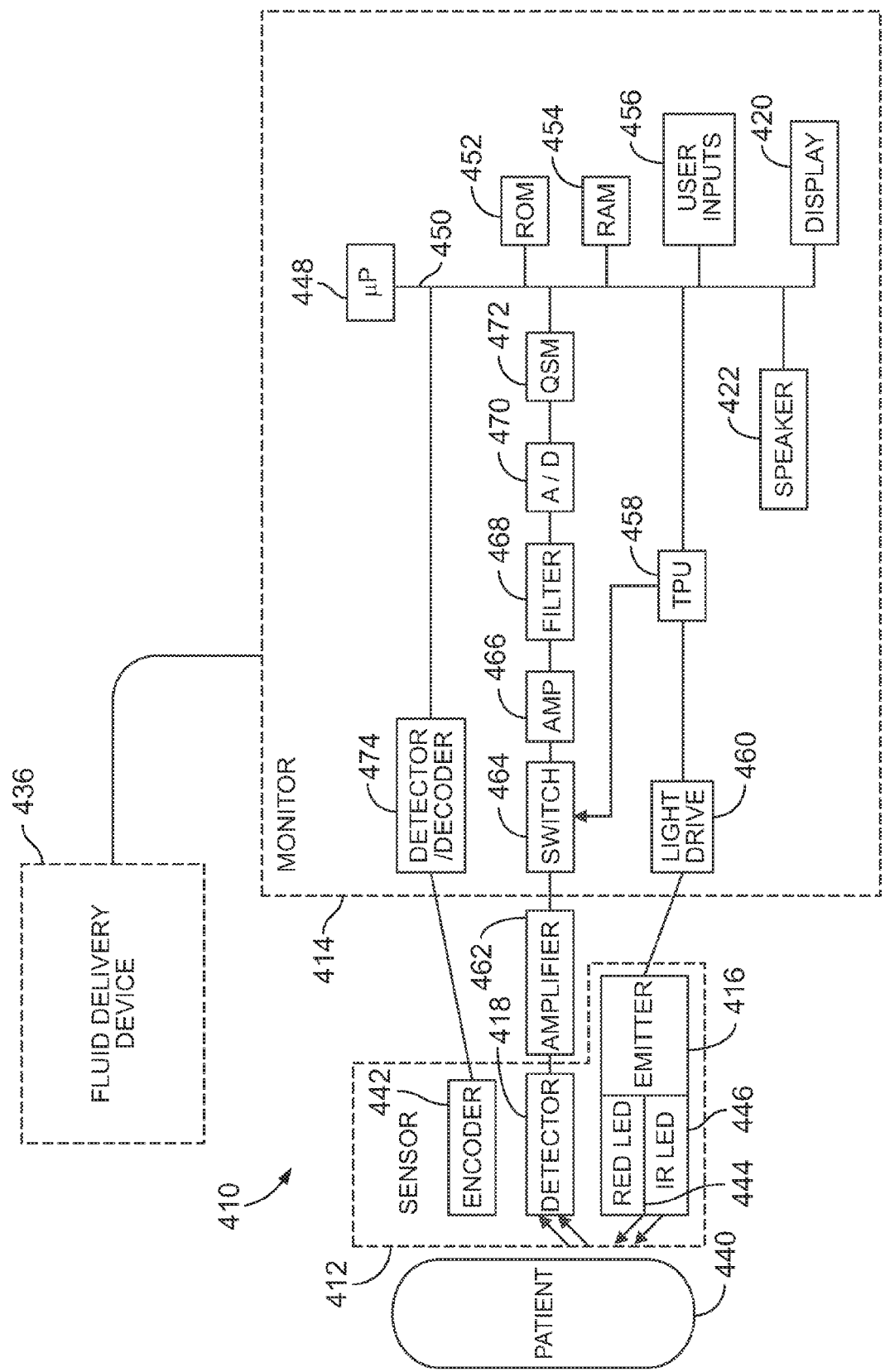
FIG. 5 illustrates a simplified block diagram of a PPG system in accordance with an embodiment.

FIG. 5 illustrates a simplified block diagram of the PPG system 410, according to an embodiment. When the PPG system 410 is a pulse oximetry system, the emitter 416 may be configured to emit at least two wavelengths of light (for example, red and infrared) into tissue 440 of a patient. Accordingly, the emitter 416 may include a red light-emitting light source such as a red light-emitting diode (LED) 444 and an infrared light-emitting light source such as an infrared LED 446 for emitting light into the tissue 440 at the wavelengths used to calculate the patient's physiological parameters. For example, the red wavelength may be between about 600 nm and about 700 nm, and the infrared wavelength may be between about 800 nm and about 1000 nm. In embodiments where a sensor array is used in place of single sensor, each sensor may be configured to emit a single wavelength. For example, a first sensor may emit a red light while a second sensor may emit an infrared light.

As discussed above, the PPG system 410 is described in terms of a pulse oximetry system. However, the PPG system 410 may be various other types of systems. For example, the PPG system 410 may be configured to emit more or less than two wavelengths of light into the tissue 440 of the patient. Further, the PPG system 410 may be configured to emit wavelengths of light other than red and infrared into the tissue 440. As used herein, the term "light" may refer to energy produced by radiative sources and may include one or more of ultrasound, radio, microwave, millimeter wave, infrared, visible, ultraviolet, gamma ray or X-ray electromagnetic radiation. The light may also include any wavelength within the radio, microwave, infrared, visible, ultraviolet, or X-ray spectra, and that any suitable wavelength of electromagnetic radiation may be used with the system 410. The detector 418 may be configured to be specifically sensitive to the chosen targeted energy spectrum of the emitter 416.

The detector 418 may be configured to detect the intensity of light at the red and infrared wavelengths. Alternatively, each sensor in the array may be configured to detect an intensity of a single wavelength. In operation, light may enter the detector 418 after passing through the tissue 440. The detector 418 may convert the intensity of the received light into an electrical signal. The light intensity may be directly related to the absorbance and/or reflectance of light in the tissue 440. For example, when more light at a certain wavelength is absorbed or reflected, less light of that wavelength is received from the tissue by the detector 418. After converting the received light to an electrical signal, the detector 418 may send the signal to the monitor 414, which calculates physiological parameters based on the absorption of the red and infrared wavelengths in the tissue 440.

In an embodiment, an encoder 442 may store information about the sensor 412, such as sensor type (for example, whether the sensor is intended for placement on a forehead or digit) and the wavelengths of light emitted by the emitter 416. The stored information may be used by the monitor 414 to select appropriate algorithms, lookup tables and/or calibration coefficients stored in the monitor 414 for calculating physiological parameters of a patient. The encoder 442 may store or otherwise contain information specific to a patient, such as, for example, the patient's age, weight, and diagnosis. The information may allow the monitor 414 to determine, for example, patient-specific threshold ranges related to the patient's physiological parameter measurements, and to enable or disable additional physiological parameter algorithms. The encoder 442 may, for instance, be a coded resistor that stores values corresponding to the type of sensor 412 or the types of each sensor in the sensor array, the wavelengths of light emitted by emitter 416 on each sensor of the sensor array, and/or the patient's characteristics. Optionally, the encoder 442 may include a memory in which one or more of the following may be stored for communication to the monitor 414: the type of the sensor 412, the wavelengths of light emitted by emitter 416, the particular wavelength each sensor in the sensor array is monitoring, a signal threshold for each sensor in the sensor array, any other suitable information, or any combination thereof.

Signals from the detector 418 and the encoder 442 may be transmitted to the monitor 414. The monitor 414 may include a general-purpose control unit, such as a microprocessor 448 connected to an internal bus 450. The microprocessor 448 may be configured to execute software, which may include an operating system and one or more applications, as part of performing the functions described herein. A read-only memory (ROM) 452, a random access memory (RAM) 454, user inputs 456, the display 420, and the speaker 422 may also be operatively connected to the bus 450.

The RAM 454 and the ROM 452 are illustrated by way of example, and not limitation. Any suitable computer-readable media may be used in the system for data storage. Computer-readable media are configured to store information that may be interpreted by the microprocessor 448. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The monitor 414 may also include a time processing unit (TPU) 458 configured to provide timing control signals to a light drive circuitry 460, which may control when the emitter 416 is illuminated and multiplexed timing for the red LED 444 and the infrared LED 446. The TPU 458 may also control the gating-in of signals from the detector 418 through an amplifier 462 and a switching circuit 464. The signals are sampled at the proper time, depending upon which light source is illuminated. The received signal from the detector 418 may be passed through an amplifier 466, a low pass filter 468, and an analog-to-digital converter 470. The digital data may then be stored in a queued serial module (QSM) 472 (or buffer) for later downloading to RAM 454 as QSM 472 fills up. In an embodiment, there may be multiple separate parallel paths having amplifier 466, filter 468, and A/D converter 470 for multiple light wavelengths or spectra received.

The microprocessor 448 may be configured to determine the patient's physiological parameters, such as $SpO_2$ and pulse rate, using various algorithms and/or look-up tables based on the value(s) of the received signals and/or data corresponding to the light received by the detector 418. The signals corresponding to information about a patient, and regarding the intensity of light emanating from the tissue 440 over time, may be transmitted from the encoder 442 to a decoder 474. The transmitted signals may include, for example, encoded information relating to patient characteristics. The decoder 474 may translate the signals to enable the microprocessor 448 to determine the thresholds based on algorithms or look-up tables stored in the ROM 452. The user inputs 456 may be used to enter information about the patient, such as age, weight, height, diagnosis, medications, treatments, and so forth. The display 420 may show a list of values that may generally apply to the patient, such as, for example, age ranges or medication families, which the user may select using the user inputs 456.

The fluid delivery device 436 may be communicatively coupled to the monitor 414. The microprocessor 448 may determine the patient's physiological parameters, such as a change or level of fluid responsiveness, and display the parameters on the display 420. In an embodiment, the parameters determined by the microprocessor 448 or otherwise by the monitor 414 may be used to adjust the fluid delivered to the patient via fluid delivery device 436.

As noted, the PPG system 410 may be a pulse oximetry system. A pulse oximeter is a medical device that may determine oxygen saturation of blood. The pulse oximeter may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of a patient. Pulse oximeters typically measure and display various blood flow characteristics including, but not limited to, the oxygen saturation of hemoglobin in arterial blood.

A pulse oximeter may include a light sensor, similar to the sensor 412, that is placed at a site on a patient, typically a fingertip, toe, forehead or earlobe, or in the case of a neonate, across a foot. The pulse oximeter may pass light using a light source through blood perfused tissue and photoelectrically sense the absorption of light in the tissue. For example, the pulse oximeter may measure the intensity of light that is received at the light sensor as a function of time. A signal representing light intensity versus time or a mathematical manipulation of this signal (for example, a scaled version thereof, a log taken thereof, a scaled version of a log taken thereof, and/or the like) may be referred to as a PPG signal. In addition, the term "PPG signal," as used herein, may also refer to an absorption signal (for example, representing the amount of light absorbed by the tissue) or any suitable mathematical manipulation thereof. The light intensity or the amount of light absorbed may then be used to calculate the amount of the blood constituent (for example, oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with lower oxygen saturation. By comparing the intensities of two wavelengths at different points in the pulse cycle, it is possible to estimate the blood oxygen saturation of hemoglobin in arterial blood.

The PPG system 410 and pulse oximetry are further described in United States Patent Application Publication No. 2012/0053433, entitled "System and Method to Determine $SpO_2$ Variability and Additional Physiological Parameters to Detect Patient Status," United States Patent Application Publication No. 2010/0324827, entitled "Fluid Responsiveness Measure," and United States Patent Application Publication No. 2009/0326353, entitled "Processing and Detecting Baseline Changes in Signals," all of which are hereby incorporated by reference in their entireties.

Figure 6:
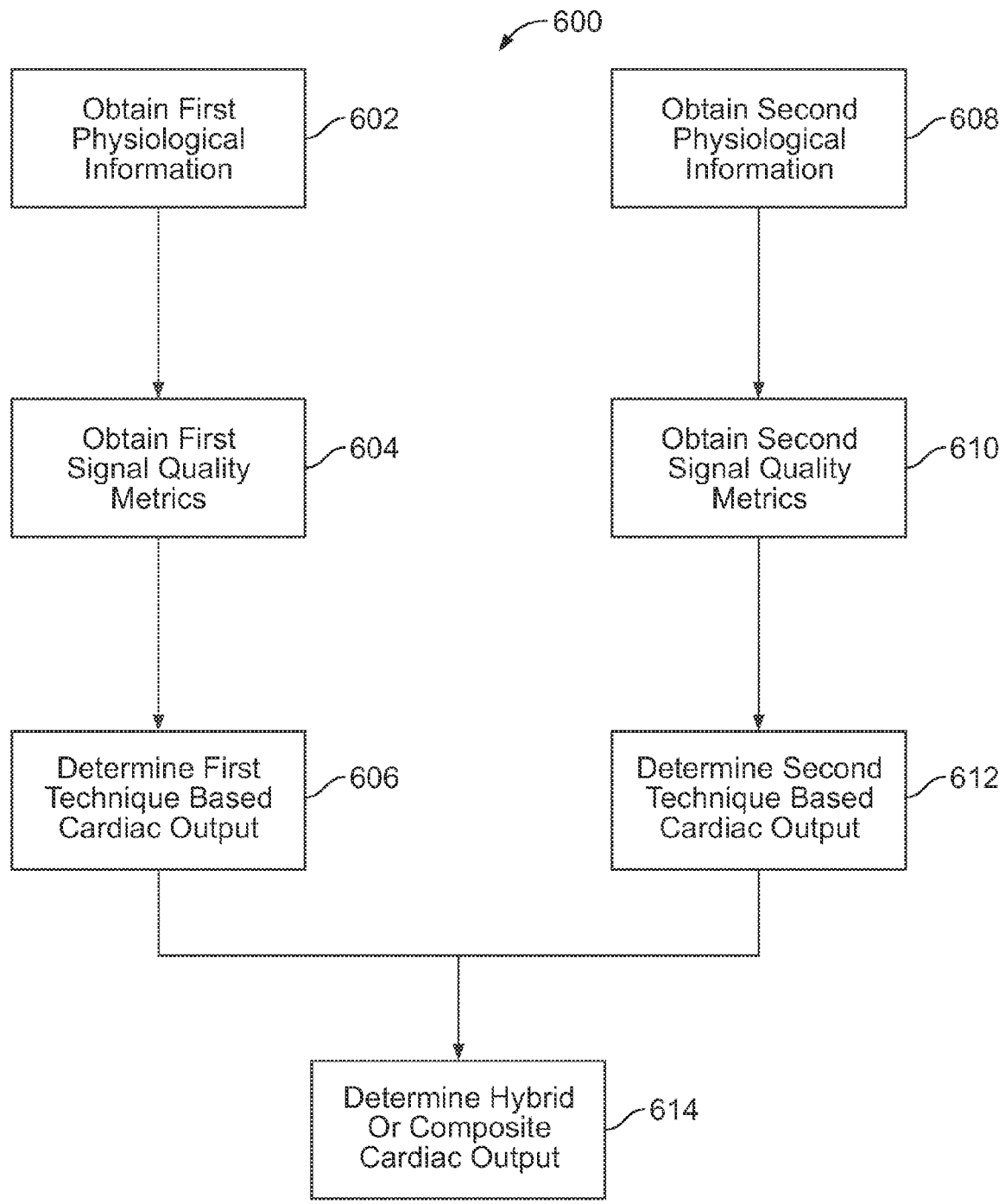
FIG. 6 illustrates a flowchart of a method for determining cardiac output according to an embodiment.

Certain embodiments provide a system and method determining cardiac output of a patient. For example, FIG. 6 provides a flowchart of a method 600 for determining cardiac output in accordance with various embodiments. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. The method 600 may be performed, for example, in association with aspects, components, systems, and/or methods such as those discussed elsewhere herein.

At 602, first physiological information is obtained by a first measurement technique. For example, the first physiological information may be TBIR information. The TBIR information may be obtained by a processing unit, such as a cardiac output module 170 and/or a TBIR analysis module 120. The TBIR information may be received from a detector such as TBIR detector 110 and/or the sensing system 300. The TBIR information corresponds to the change of impedance in the thorax of a patient, which in turn corresponds to the change of blood volume in the thorax. Thus, the TBIR information may be used to provide information regarding the amount of blood being drawn into and ejected from the heart during a cardiac cycle (e.g., stroke volume).

At 604, first signal quality metrics are obtained. For example, the signal quality metrics may be determined by a TBIR analysis module 120 from an analysis of the obtained TBIR information and/or patient information provided by a patient information module 109. Signal quality metrics may include a signal-to-noise ratio for the TBIR information. Also, signal quality metrics may include metrics corresponding to patient characteristics (such as obesity) or metrics corresponding to a particular detection system being employed. The signal quality metrics may also include metrics comparing the amount of match or fit between the obtained TBIR information and expected TBIR information, such as an amount of match or fit of an obtained TBIR waveform with the expected shape of a TBIR waveform.

At 606, a first technique-based cardiac output is determined, for example by a TBIR analysis module 120. The first technique-based cardiac output may correspond to the cardiac output over a given duration of time, for example about one minute. In some embodiments, the TBIR-based cardiac output may be determined by using empirically determined formula (e) or table(s) to determine a stroke volume based on the TBIR information and MAP obtained by a blood pressure detector 150. The TBIR-based cardiac output may then be determined by multiplying the stroke volume by the pulse rate. The pulse rate may be determined, for example, using PPG information provided by a PPG detector 140.

At 608, second physiological information is obtained by a second measurement technique. For example, the second physiological information may be PPG information. The PPG information may be obtained by a processing unit, such as a cardiac output module 170 and/or a PPG analysis module 140. The PPG information may be received from a detector such as the PPG detector 130. The second physiological information may obtained substantially concurrently with the first physiological information.

At 610, second signal quality metrics are obtained. For example, the signal quality metrics may be determined by a PPG analysis module 140 from an analysis of the obtained PPG information and/or patient information provided by a patient information module 109. Signal quality metrics may include a signal-to-noise ratio for the PPG information. Also, signal quality metrics may include metrics corresponding to patient characteristics (such as whether or not the patient is taking medication that may affect the measured PPG), metrics indicating the presence, absence or amount of artifacts such as motion of a finger to which a pulse oximeter is attached, or metrics corresponding to a particular detection system being employed. The signal quality metrics may also include metrics comparing the amount of match or fit between the obtained PPG information and expected PPG information, such as an amount of match or fit of an obtained PPG waveform with the expected shape of a PPG waveform (e.g., how well the obtained PPG waveform conforms with an expected double bump profile as depicted in FIG. 2*a*).

At 612, a second technique-based cardiac output is determined, for example by a PPG analysis module 140. The second technique-based cardiac output may correspond to the cardiac output over a given duration of time, for example about one minute. In some embodiments, the PPG-based cardiac output (or value such as SVR used to determine the PPG-based cardiac output) may be determined by using empirically determined formula (e) or table(s) using one or more ratios comparing the primary peak of a PPG waveform with a trailing peak of the PPG waveform. The second technique-based cardiac output may be determined substantially concurrently with the first technique-based cardiac output, thus allowing for a comparison or combination of the technique-based cardiac outputs for a given period of time.

At 614, a hybrid or composite cardiac output is determined using the first and second technique-based cardiac outputs and the first and second signal quality metrics. The cardiac output may be determined at a processing unit, such as the cardiac output module 170. The cardiac output may be determined by selecting the technique-based cardiac output having more favorable signal quality metrics from the first and second technique-based cardiac outputs. For example, if the second technique-based cardiac output has poor signal quality metrics associated therewith (e.g., an indication of substantial motion artifacts, a poor match with an expected shape of a waveform, or an indication that a patient has a medical condition or is taking medication that may confound a measurement technique associated with the second technique-based cardiac output), then the second technique-based cardiac output may be discarded and the first technique-based cardiac based output selected. Alternatively or additionally, the first and second technique-based cardiac outputs may be combined, with each technique-based cardiac output weighted in the combination according to the relative quality of corresponding signal quality metrics. For example, if each of the first and second signal quality metrics satisfy a particular threshold, the first and second cardiac outputs may be combined, while if one does not satisfy a particular threshold, the other may be selected without combining the two.

Figure 7:
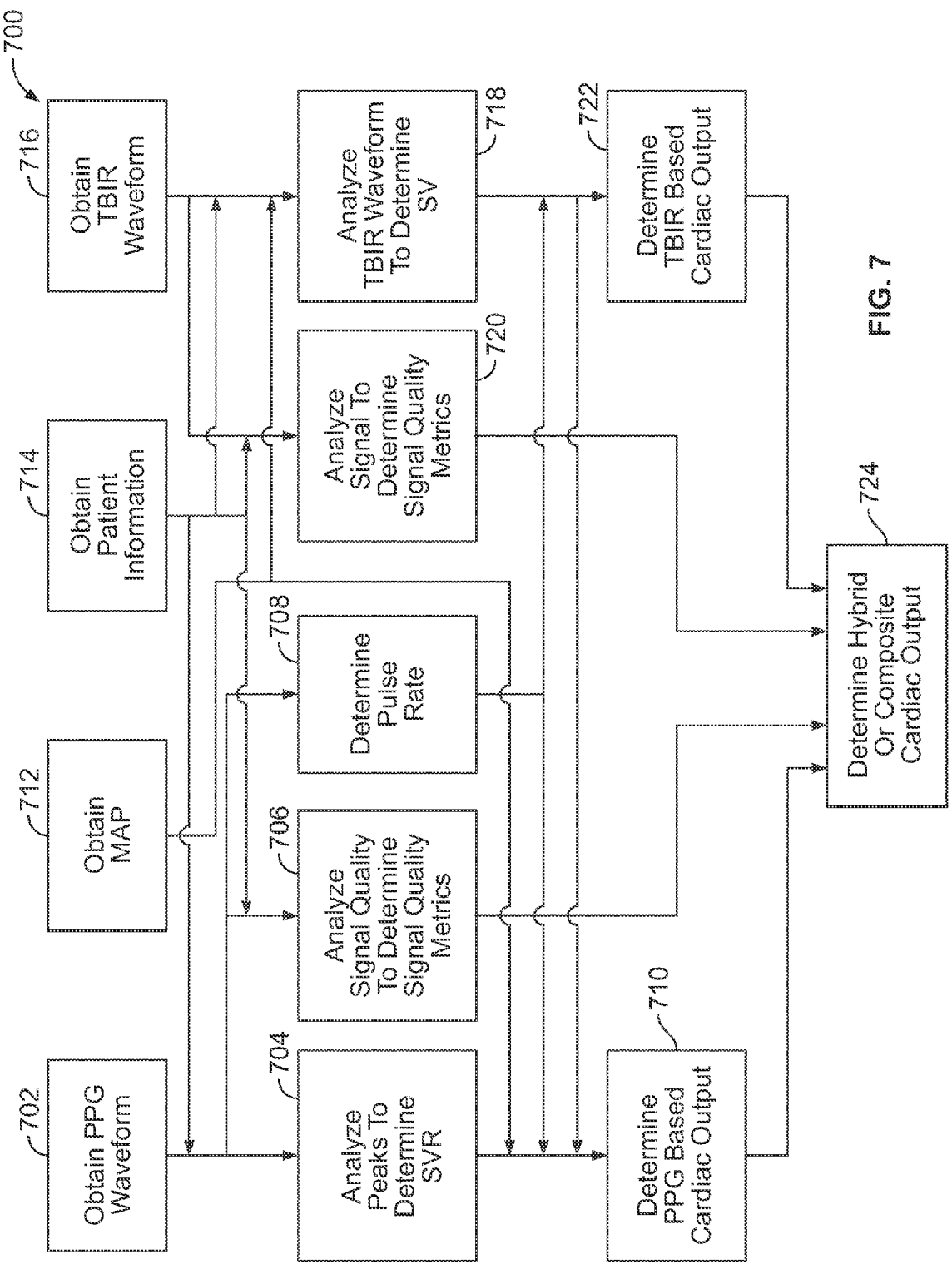
FIG. 7 illustrates a flowchart of a method for determining cardiac output according to an embodiment.

FIG. 7 illustrates a flowchart of a method 700 for determining fluid responsiveness in accordance with various embodiments. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. For example, steps depicted at a given level vertically in FIG. 7 may be performed substantially concurrently with steps depicted at the same vertical level. The method 700 may be performed, for example, in association with aspects, components, systems, and/or methods such as those discussed elsewhere herein.

At 702, a PPG waveform (see, e.g., FIG. 2b and related discussion) is obtained. For example, the PPG waveform may be determined by a PPG analysis module 140 using information obtained by a PPG detector 120. The PPG waveform may be utilized to determine a PPG-based cardiac output.

At 704, the relative sizes (e.g., height and/or area) of the primary and trailing peaks (see, e.g., FIG. 2b and related discussion) are analyzed to determine a systemic vascular resistance (SVR). For example, one or more ratios corresponding to the relative sizes of the primary and trailing peaks may be computed by the PPG analysis module 140. The PPG analysis module may then determine the SVR using, for example, an empirically determined formula or look-up table, or, as another example, a neural network trained during a clinical study. The empirically determined analysis may also use information from a patient data system, for example, to select an appropriate formula or look up table based on a demographic group or groups to which the patient belongs. The PPG analysis module 140 may also use information obtained by one or more other detectors to determine SVR. For example, an SVR determined using information from a TBIR detector 110 may be used in combination with an SVR determined using a PPG-based approach to provide a composite SVR.

At 706, the PPG signal quality is analyzed to provide PPG signal quality metrics. For example, the PPG analysis module 140 may analyze the PPG information to determine a signal-to-noise ratio. As another example, the PPG analysis module 140 may determine a signal quality metric based on a comparison of an obtained PPG waveform with an expected PPG waveform, using an amount of match or fit of the shape of the obtained waveform with the expected shape to determine a signal quality metric.

At 708, a pulse rate is determined. For example, the pulse rate may be determined by the PPG analysis module 140 based on the time between primary peaks in the PPG waveform.

At 710, a PPG-based cardiac output is determined. The PPG-based cardiac output may correspond to the cardiac output over a given duration of time, for example about one minute. For example, the PPG-based cardiac output may be determined using the relationship CO (cardiac output)=PR (pulse rate)×SV (stroke volume), where the stroke volume is determined using the relationship SV=PR×SVR (systemic vascular resistance)/MAP (mean arterial pressure).

MAP, for example, may be obtained by a blood pressure detector, such as blood pressure detector 150, at 712. The obtained MAP may be used, for example, in determining both the PPG-based cardiac output as well as the TBIR-based cardiac output.

At 714, patient information is obtained. For example, patient information may be provided by a patient information module 109. The patient information may include, for example, information on a demographic group or groups to which the patient belongs, such as information corresponding to the age, height, weight, or gender of the patient. The patient information may also include any specific conditions in the patient's medical history and/or any medications the patient is currently taking that may affect one or more sensed or detected measurements. The patient information obtained at 714 may be utilized in determining the PPG-based cardiac output and/or the TBIR-based cardiac output as well as corresponding signal quality metrics. For example, a demographic group to which the patient belongs may be used in selecting an appropriate empirically derived formula or look-up table used in determining a technique-based cardiac output.

At 716, a TBIR waveform (see, e.g., FIG. 2a and related discussion) is obtained. For example, the TBIR waveform may be determined by a TBIR analysis module 120 using information obtained by a TBIR detector 110. The TBIR waveform may be utilized to determine a TBIR-based cardiac output.

At 718, the TBIR waveform is analyzed to determine stroke volume. For example, the difference between a peak and a bottom of the TBIR waveform (see, e.g., FIG. 2a and related discussion) provides information corresponding to the volume of blood moving through the thorax and may be correlated to the stroke volume. For example, the TBIR analysis module 120 may determine the stroke volume, for example, using an empirically determined formula or look-up table that correlates the change in measured impedance to stroke volume, or, as another example, using a neural network trained during a clinical study. The empirically determined technique may also use MAP obtained at 712 as an input. The empirically determined analysis may also use information from a patient data system, for example, to select an appropriate formula or look up table based on a demographic group or groups to which the patient belongs.

At 720, the TBIR signal quality is analyzed to provide TBIR signal quality metrics. For example, the TBIR analysis module 120 may analyze the TBIR information to determine a signal-to-noise ratio. As another example, the TBIR analysis module 120 may determine a signal quality metric based on a comparison of an obtained TBIR waveform with an expected TBIR waveform, using an amount of match or fit of the shape of the obtained waveform with the expected shape to determine a signal quality metric.

At 722, a TBIR-based cardiac output is determined using the relationship CO (cardiac output)=PR (pulse rate)×SV (stroke volume). The TBIR-based cardiac output may be determined by the TBIR analysis module using information obtained from both the TBIR detector 110 and the PPG detector 130. For example, the SV may be determined using information from the TBIR detector as discussed above, and the PR may be determined using information from the PPG detector 130. The TBIR-based cardiac output may correspond to the cardiac output over a given duration of time, for example about one minute.

At 724, a hybrid or composite cardiac output is determined using the PPG and TBIR-based cardiac outputs and the corresponding signal quality metrics. The hybrid or composite cardiac output may be determined by selecting the technique-based cardiac output having more favorable signal quality metrics. For example, if the PPG-based cardiac output has poor signal quality metrics associated therewith (e.g., an indication of substantial motion artifacts, a poor match with an expected shape of a PPG waveform, or an indication that a patient has a medical condition or is taking medication that may confound a PPG measurement), then the PPG-based cardiac output may be discarded and the TBIR-based output selected. Alternatively or additionally, the PPG and TBIR-based cardiac outputs may be combined, with each technique-based cardiac output weighted in the combination according to the relative quality of corresponding signal quality metrics. For example, if each of the PPG and TBIR signal quality metrics satisfy a particular threshold, the PPG and TBIR-based cardiac outputs may be combined, while if one does not satisfy a particular threshold, the other may be selected without combining the two. Further, in some embodiments, the weightings used in combining the PPG and TBIR-based cardiac outputs may be empirically determined. For example, a neural network may be trained during a clinical study during which cardiac output is determined using invasive means while PPG information, TBIR information, and corresponding signal quality metrics are concurrently recorded. The neural network may be trained during the clinical study to use the PPG-based and TBIR-based cardiac outputs (or other PPG and TBIR information) along with corresponding signal quality metrics as inputs to arrive at the cardiac output.

Thus, embodiments and system according to various embodiments provide for improved determination of cardiac output using non-invasive methods. For example, a first technique-based cardiac output may be determined using a first type of detected information (e.g., TBIR information) and a second technique-based cardiac output may be determined using a second type of detected information (e.g., PPG information). The technique-based cardiac outputs may then be combined by either a comparison or combination based on respective signal quality metrics. Because different confounding events or circumstances may affect the technique-based output differently, using a variety of techniques and selecting (or weighting more heavily) the technique having better signal quality metrics, an improved cardiac output may be determined. Further, in some embodiments, information obtained by one or more techniques (e.g., TBIR, PPG) may also be utilized in determining a cardiac output based on one or more additional techniques, thereby improving the technique-based results as well.

The various systems, monitors, modules, and units disclosed herein may include a controller, such as a computer processor or other logic-based device that performs operations based on one or more sets of instructions (e.g., software). The instructions on which the controller operates may be stored on a tangible and non-transitory (e.g., not a transient signal) computer readable storage medium, such as a memory. The memory may include one or more computer hard drives, flash drives, RAM, ROM, EEPROM, and the like. Alternatively, one or more of the sets of instructions that direct operations of the controller may be hard-wired into the logic of the controller, such as by being hard-wired logic formed in the hardware of the controller.

The various embodiments and/or components, for example, the modules, monitors, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. For example, a module or system may include a computer processor, controller, or other logic-based device that performs operations based on instructions stored on a tangible and non-transitory computer readable storage medium, such as a computer memory. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. While the dimensions, types of materials, and the like described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A method for determining a cardiac output of a patient comprising:
   obtaining a thoracic bio-impedance or bio-reactance (TBIR) signal from a TBIR detector configured to detect TBIR activity of the patient;
   electronically measuring a voltage of the TBIR signal to determine an impedance value;
   determining a first cardiac output value for the patient from a change in the impedance value over a heart cycle;
   obtaining a photoplethysmographic (PPG) signal from a PPG detector configured to detect PPG activity of the patient;
   calculating a ratio of first and second peaks in the PPG signal;
   determining a second cardiac output value for the patient from the ratio;
   determining, at a processor, a subsequent cardiac output of the patient from the first and second cardiac output values.

2. The method of claim 1, wherein the subsequent cardiac output of the patient is determined using at least one of a comparison or a combination of the first and second cardiac output values.

3. The method of claim 2, further comprising:
   obtaining TBIR signal quality information corresponding to a quality of the TBIR signal; and
   obtaining PPG signal quality information corresponding to a quality of the PPG signal;
   wherein the at least one of the comparison or the combination is performed using the TBIR signal quality information and the PPG signal quality information.

4. The method of claim 1, wherein
   determining the first cardiac output value includes using a pulse rate determined at least in part from the PPG signal.

5. The method of claim 1, further comprising obtaining blood pressure information from a blood pressure detector, wherein
   determining the second cardiac output value includes using the blood pressure information obtained from the blood pressure detector.

6. The method of claim 1, wherein the subsequent cardiac output of the patient is determined using a combination of the first and second cardiac output values.

7. The method of claim 6, wherein the combination comprises a weighted combination.

8. The method of claim 7, wherein a weight for the weighed combination is based on one or more signal quality metrics of the TBIR signal or the PPG signal.

9. The method of claim 1, wherein the subsequent cardiac output of the patient is determined using a comparison of the first and second cardiac output values.

10. The method of claim 3, wherein the TBIR signal quality information comprises a signal to noise ratio.

11. The method of claim 3, wherein the TBIR signal quality information comprises a presence or amount of artifact.

12. The method of claim 3, wherein the TBIR signal quality information comprises information about a positive end expiratory pressure.

13. The method of claim 3, wherein the TBIR signal quality information comprises a physiologic condition of the patient.

14. The method of claim 3, wherein the TBIR signal quality information comprises an amount of match between the obtained TBIR signal and an expected characteristic of the TBIR signal.

15. The method of claim 3, wherein the PPG signal quality information comprises a signal to noise ratio.

16. The method of claim 3, wherein the PPG signal quality information comprises a presence or amount of artifact.

17. The method of claim 3, wherein the PPG signal quality information comprises a physiologic condition of the patient.

18. The method of claim 3, wherein the PPG signal quality information comprises an amount of match between the obtained PPG signal and an expected characteristic of the PPG signal.

19. The method of claim 1, wherein the subsequent cardiac output of the patient is determined using a selection of the first cardiac output value or the second cardiac output value.

20. The method of claim 1, wherein determining the first cardiac output value from the change in the impedance value comprises utilizing an empirically derived relationship.

21. The method of claim 1, wherein determining the second cardiac output value from the ratio comprises utilizing an empirically derived relationship.

22. The method of claim 1 further comprising obtaining blood pressure information from a blood pressure detector, and using the blood pressure information to determine the subsequent cardiac output of the patient.

* * * * *